(12) United States Patent
Ericson et al.

(10) Patent No.: US 6,601,432 B1
(45) Date of Patent: Aug. 5, 2003

(54) METHOD AND APPARATUS FOR CHECKING SENSORS

(75) Inventors: Bjorn Ericson, Lund (SE); Per-Ola Wictor, Stehag (SE)

(73) Assignee: Gambro AB, Stockholm (SE)

( * ) Notice: Subject to any disclaimer, the term of this patent is extended or adjusted under 35 U.S.C. 154(b) by 0 days.

(21) Appl. No.: 09/889,060

(22) PCT Filed: Jan. 11, 2000

(86) PCT No.: PCT/SE00/00029
§ 371 (c)(1),
(2), (4) Date: Jul. 11, 2001

(87) PCT Pub. No.: WO00/42406
PCT Pub. Date: Jul. 20, 2000

(30) Foreign Application Priority Data

Jan. 14, 1999 (SE) .................................. 9900077

(51) Int. Cl.⁷ .................................. G01L 7/00
(52) U.S. Cl. .................................. 73/1.58
(58) Field of Search .................. 73/1.57–1.59, 73/1.61–1.64

(56) References Cited

U.S. PATENT DOCUMENTS

| | | | |
|---|---|---|---|
| 596,581 A | 1/1898 | Edson | |
| 3,557,602 A | 1/1971 | Frantz | |
| 4,111,058 A | 9/1978 | Gross | |
| 4,189,936 A | 2/1980 | Ellis | |
| 4,664,635 A | * 5/1987 | Hermann | 73/1.64 |
| 4,753,105 A | 6/1988 | Juanarena et al. | |
| 5,402,666 A | 4/1995 | Chalpin | |
| 5,479,813 A | 1/1996 | Pla et al. | |
| 5,753,820 A | 5/1998 | Reed et al. | |

FOREIGN PATENT DOCUMENTS

FR   2532761   3/1984

* cited by examiner

Primary Examiner—Robert Raevis

(57) ABSTRACT

Methods and apparatus are disclosed for testing differential pressure sensors. The method includes applying a pressure of predetermined value to the reference side of the differntial pressure sensors, measuring the output values from the measurement sides of the differential pressure sensors, and comparing the measured output values. The disclosed apparatus includes a pump for simultaneously applying a pressure of a predetermined value to the reference side of a number of differential pressure sensors.

3 Claims, 2 Drawing Sheets

METHOD AND APPARATUS FOR CHECKING SENSORS

FIELD OF THE INVENTION

The present invention relates to a method and apparatus for testing sensors of the type for measuring a specific quantity. More particularly, the present invention relates to a method for testing differential pressure sensors in an apparatus for the extracorporeal treatment of blood, such as a dialysis monitor.

BACKGROUND OF THE INVENTION

In apparatus for the extracorporeal treatment of blood, there are usually arranged several identical sensors for measuring a specific quantity. This is intended to achieve improved control and monitoring, as well as increased safety. For example, a dialysis monitor comprises several sensors for measuring the pressure in fluid conduits utilized during dialysis.

On the one hand, these fluid conduits transport blood from the patient to the blood side of the dialyser and from there back to the patient and, on the other hand, they transport dialysis fluid from the dialysis fluid source to the dialysate side of the dialyser, and from there to an outlet. The blood-carrying conduits are generally exchanged after each treatment, while the conduits transporting the dialysis fluid are permanently connected to the dialysis monitor and are disinfected and rinsed after each treatment.

The monitoring of pressure during dialysis, both in the blood-carrying conduits and in the conduits carrying the dialysis fluid, is important for several reasons. One important reason is, for example, surveillance of the transmembrane pressure at the membrane present in the dialyser that separates dialysis fluid from blood, and which is semi-permeable. This transmembrane pressure is the pressure difference between the pressure on the blood side and the pressure on the dialysate side, and determines the direction and quantity of fluid transport through the membrane. If the transmembrane pressure is positive, then the fluid will be drawn out of the blood. This process is also called ultrafiltration. With a negative transmembrane pressure no excess fluid will be drawn from the patient. The removal of excess fluid is, however, one of the principal functions of dialysis, so that the importance of monitoring the pressure in the dialysis fluid conduits and blood conduits is evident from this alone.

A further important reason is monitoring of the arterial and venal pressure in the blood-carrying conduits during treatment. If, for example, the arterial pressure should be below a specific negative pressure, then the arterial needle could be blocked or lodged in the fistula wall, or the conduit could be folded over. In order to avoid damage to the fistula, the machine will automatically be stopped, and an alarm triggered. If the arterial pressure exceeds a predetermined negative pressure, then the arterial needle could have come loose and be sucking in air. In this case also an alarm will automatically be triggered, and the machine stopped.

On the other hand, if the venal pressure should fall below a predetermined value, then the blood feedback to the patient could be not sealed or interrupted. If the venal pressure exceeds a specific predetermined value, then the venal needle could be blocked, or the feedback tube bent. In this case the machine will likewise be stopped, and an alarm automatically triggered.

However, in order to reliably monitor the pressure, operation of the sensors must be trouble-free. These are thus checked prior to operation of the dialysis monitor during a check phase, in which a functional check of the entire dialysis monitor takes place.

Thus, for checking the sensors that measure the pressure in the dialysis fluid conduits (hereinafter referred to as dialysate pressure sensors), at least two of which are provided, a static pressure is generated in these conduits. For the present case, static pressure means that the dialysis fluid does not flow through the conduits, but rather sits in the conduits, and that a pressure is applied to the stationary dialysis fluid. In this way, the effects on the pressure measurement of the valves, throttles, pumps, etc. that are arranged in the tubes, are excluded. The values supplied by the individual dialysate pressure sensors are compared with one another; the individual dialysate pressure sensors must all supply the same value, as they are subjected to the same pressure.

If the individual dialysate pressure sensors supply different values, then a sensor malfunction has occurred, and the control or monitoring unit of the dialysis monitor generates a corresponding alarm.

The pressure sensors generally used in this case are so-called differential pressure sensors that utilize atmospheric pressure as a reference value. These sensors are checked by applying two different static pressures in the described manner, one generally being positive with respect to atmospheric pressure and one being negative with respect to atmospheric pressure. On the one hand, the values supplied by the sensors are compared with one another in order to determine a possible sensor malfunction. On the other hand, the values supplied by each individual sensor at the different pressures are also used to determine the constant allocated to each individual sensor. This constant is necessary for precise determination of the pressure, and can be determined only with the aid of at least two values supplied at different pressures.

The sensors that measure the pressure in the blood conduits, of which at least two are provided, (hereinafter referred to as blood pressure sensors) are usually also differential pressure sensors. In contrast to the dialysate pressure sensors that are permanently connected with the dialysis fluid conduit, the blood pressure sensors are not permanently connected to the blood conduits. As mentioned above, new blood conduits are used for each treatment, so that the blood pressure sensors must be connected to the blood conduits by the operating personnel before each treatment. During the check phase before the treatment, the blood pressure sensors are generally not connected to the blood conduits, thus no pressure or different pressures may be generated in the blood conduits and applied to the blood pressure sensors for testing same. It is, therefore, only possible to examine whether the blood pressure sensors each supply the same reference value corresponding to atmospheric pressure. However, this provides no information as to whether the blood pressure sensors will supply the same values at the same applied pressure above or below atmospheric pressure.

It is possible to test the blood pressure sensors during the check or test phase by connecting the blood pressure sensors with a separate conduit and to generate one predetermined pressure, or different predetermined pressures, in this conduit. However, this requires, on the one hand a supplementary material complexity, as the dialysis monitor must be correspondingly adapted to enable this additional test option. Furthermore, additional, specially constructed conduits are necessary, so that the material complexity and the cost as a whole increases. On the other hand, the operating complexity for the operating personnel is markedly increased as, in the test phase, the operating personnel must first attach the special test tube to the dialysis monitor and connect it to the blood pressure sensors. After completing the test, the operating personnel must then remove the special test tube before the blood conduits and the dialyser can be connected to the dialysis monitor, and the blood pressure sensors can be connected to the blood conduits.

In view of this background, it is an object of the present invention to provide a method and apparatus for testing identical sensors for measuring a specific quantity, in particular for checking differential pressure sensors with a reference side and a measurement side, with which these disadvantages can be alleviated.

In particular, testing of the blood pressure sensors of dialysis monitors without additional manipulation by the operating personnel, and without the attachment of separate tubes to the dialysis monitor that need removing after testing, should be made possible.

SUMMARY OF THE INVENTION

In accordance with the present invention, these and other objects have now been realized by the invention of a method for testing a plurality of differential pressure sensors, each of the plurality of differential pressure sensors including a reference side and a measurement side, the method comprising applying a pressure having a predetermined value to the reference side of the plurality of differential pressure sensors, measuring the output values from the measurement side for each of the plurality of differential pressure sensors, and comparing the plurality of measured output values. Preferably, the predetermined value comprises a positive pressure value. In another embodiment, the predetermined value comprises a negative pressure value.

In accordance with one embodiment of the method of the present invention, the predetermined value comprises a first predetermined value, and the method includes applying a pressure having a second predetermined value to the reference side of the plurality of differential pressure sensors. Preferably, one of the first and second predetermined values comprises a positive pressure value and the other of the first and second predetermined values comprises a negative pressure value.

In accordance with one embodiment of the method of the present invention, the method includes applying the pressure by means of a pump.

In accordance with another embodiment of the method of the present invention, applying of the pressure is carried out in an apparatus for the extracorporeal treatment of blood. Preferably, applying the pressure is carried out in a dialysis monitor.

In accordance with the present invention, these objects have also been realized by the invention of apparatus for testing a plurality of differential pressure sensors, each of the plurality of differential pressure sensors including a reference side and a measurement side, the apparatus comprising pressure means for simultaneously applying a pressure having a predetermined value to the reference side of the plurality of differential pressure sensors. Preferably, the pressure means comprises pressure generating means. In a preferred embodiment, the apparatus includes connection means for connecting the pressure generating means to the plurality of differential pressure sensors. Preferably, the connecting means comprises tube means, preferably comprising pipe means.

In accordance with one embodiment of the apparatus of the present invention, the pressure means comprises a pump. In a preferred embodiment, the pump is selected from the group consisting of a plunger pump and a peristaltic pump.

In accordance with one embodiment of the apparatus of the present invention, the connection means comprises permanent connection means.

In accordance with another embodiment of the apparatus of the present invention, the connection means connects the pressure generating means to the plurality of differential pressure sensors solely for testing the differential pressure sensors. Preferably, the connection means includes an equalization opening dimensioned such that the pressure means can apply the pressure having the predetermined value to the reference sides of the plurality of differential pressure sensors and the surrounding pressure can be applied to the reference sides of the plurality of differential pressure sensors as a reference value.

The objects of the present invention are achieved by a method, wherein a pressure of predetermined value is applied simultaneously to the reference side of the sensors, and the output values of the sensors are compared with one another.

In this manner, a simple and reliable method is provided, with which the functional capability of differential pressure sensors can be determined with certainty. If a predetermined pressure value is applied simultaneously, for example, to the reference side of the blood pressure sensors in a dialysis monitor, then these must supply the same output value, or the same increase or decrease in output value, if they are functioning correctly. By comparing the output values of the sensors, the functioning of the sensors can, therefore, easily be verified. If the blood pressure sensors supply the same output value, or the same increase or decrease in output value, then no malfunction has occurred. However, if the blood pressure sensors supply different output values, or different variations in output value, then a malfunction has occurred and corresponding measures for removing the error can be applied.

The pressure values applied during this process can be of any desired magnitude and should advantageously lie in the working range, or measurement range, of the utilized differential pressure sensors. For example, the pressure value can be a positive or a negative value.

However, when using two different pressure values, on the one hand, the precision of the test can be increased, and on the other hand, the constant associated with each pressure sensor can be determined, as already described in detail above. The constant associated with each differential pressure sensor is necessary for exact determination of the pressure and can be determined only with the aid of at least two measurement values. Thus, according to a preferred embodiment of the present invention, two different predetermined pressure values are successively applied to the reference side of the differential pressure sensors.

These different pressure values can be any desired pressure value, but advantageously a pressure that is positive relative to atmospheric pressure and a pressure that is negative relative to atmospheric pressure are applied successively, wherein either the positive or the negative pressure can be applied first. This is particularly advantageous for blood pressure sensors in a dialysis monitor which must measure both the negative arterial pressure and the positive venal pressure in the blood carrying conduits, so that the working range of the sensors is tested.

The pressure applied to the reference side for testing the differential pressure sensors can be generated by any appropriate means. However, the means should be selected such that they generate a pressure lying in the working, or measurement, range of the differential pressure sensors. Advantageously, the pressure is generated by means of a pump, as large pressure ranges can be covered thereby.

With the method according to the present invention, differential pressure sensors that are arranged in an apparatus for the extracorporeal treatment of blood can advantageously also be tested. In these apparatus, and particularly in dialysis monitors, there are inter alia generally several differential pressure sensors provided for measuring the pressure in the blood tubes. With the method according to the present invention, for example, these blood pressure sensors can be easily tested, without large additional effort by the operating personnel and without large supplementary material costs.

The objects of the present invention are achieved by means of an apparatus, wherein the apparatus comprises means for simultaneously applying a predetermined pressure to the reference side of the sensors.

In this manner, simple and reliable apparatus is provided, with which the functional capability of differential pressure sensors can be determined with certainty. If a predetermined pressure is applied simultaneously to the reference side of, for example, the blood pressure sensors in a dialysis monitor with the aid of the means, then the sensors should supply the same output value, or increase or decrease in output value, when functioning correctly. As described above in detail with reference to the solution in the form of a method, the function of the blood pressure sensors can be easily checked by comparing the output values of the sensors with one another.

The apparatus does not need to include means for generating the pressure itself, although this is provided according to a preferred embodiment. The means for generating the pressure itself can take any desired form, provided that they ensure generation of the required pressure. Advantageously, however, the means for generating the pressure comprise a pump, so that large pressure ranges may be covered. According to a particularly preferred embodiment, the pump is a plunger pump or a peristaltic pump, which, for example, is widely used in the field of medicine.

The means for simultaneously applying the predetermined pressure value to the reference side of the sensors can take any desired form, provided that they ensure simultaneous application to the reference side. However, advantageously, the means for simultaneous application comprise means for connecting the sensors with means for generating the pressure. In this manner, it is possible to apply the generated pressure directly to the reference side of the sensors. According to a further preferred embodiment, therefore, means for connecting the sensors with means for generating the pressure comprise tubes, while according to another preferred embodiment they comprise pipes.

These pipes or tubes can permanently connect the means for generating the pressure with the sensors, which is advantageous when, for example, the apparatus for testing the sensors is to be permanently arranged in a dialysis monitor. This offers the advantage that the blood pressure sensors can be checked at any time by the operating personnel, without additional manipulation. This means not only that the blood pressure sensors can be automatically tested in the test phase of the dialysis monitor prior to dialysis treatment but, for example, also during the dialysis treatment itself, or during short interruptions in the treatment, during which the dialysis monitor is checked and calibrated. Thus, a further preferred embodiment provides that the pipes or tubes permanently connect the means for generating the pressure with the sensors.

However, when manipulation by the operating personnel is taken into account, it is also possible to connect means for generating the pressure with the sensors by means of pipes or tubes only for the purpose of testing the sensors. This is useful, for example, when one apparatus for testing sensors is to be used with several devices, such as dialysis monitors. This flexible utilisation of the apparatus for testing sensors is, therefore, provided in accordance with another preferred embodiment, in which the means for connecting the sensors with the means for generating the pressure values only connect the means for generating the pressure values with the sensors for the purpose of testing the sensors.

The atmospheric, or surrounding, pressure that acts on the reference side of the differential pressure sensors and is utilized as a reference value for the differential pressure sensors can be applied to the reference side in any desired manner. However, it is advantageous when the atmospheric, or surrounding, pressure also reaches the reference side through the connecting means, as this provides a defined access to the reference side. At the same time, the connecting means can comprise an equalisation opening that is dimensioned such that, on the one hand, the predetermined pressure can be applied to the reference side by the means for generating the pressure, and on the other hand, the surrounding pressure can be applied to the reference side as a reference value. This is advantageous when the means for generating the pressure closes the connecting means, so that, apart from the equalisation opening, the reference side of the sensors has no direct connection to the surroundings, which, for example, is the case for a peristaltic or plunger pump. In this case, the equalisation opening provides a defined connection to the surroundings.

DESCRIPTION OF THE DRAWINGS

In the following detailed description, the present invention will be described in more detail with reference to the enclosed drawings, in which.

DETAILED DESCRIPTION

Figure 1:
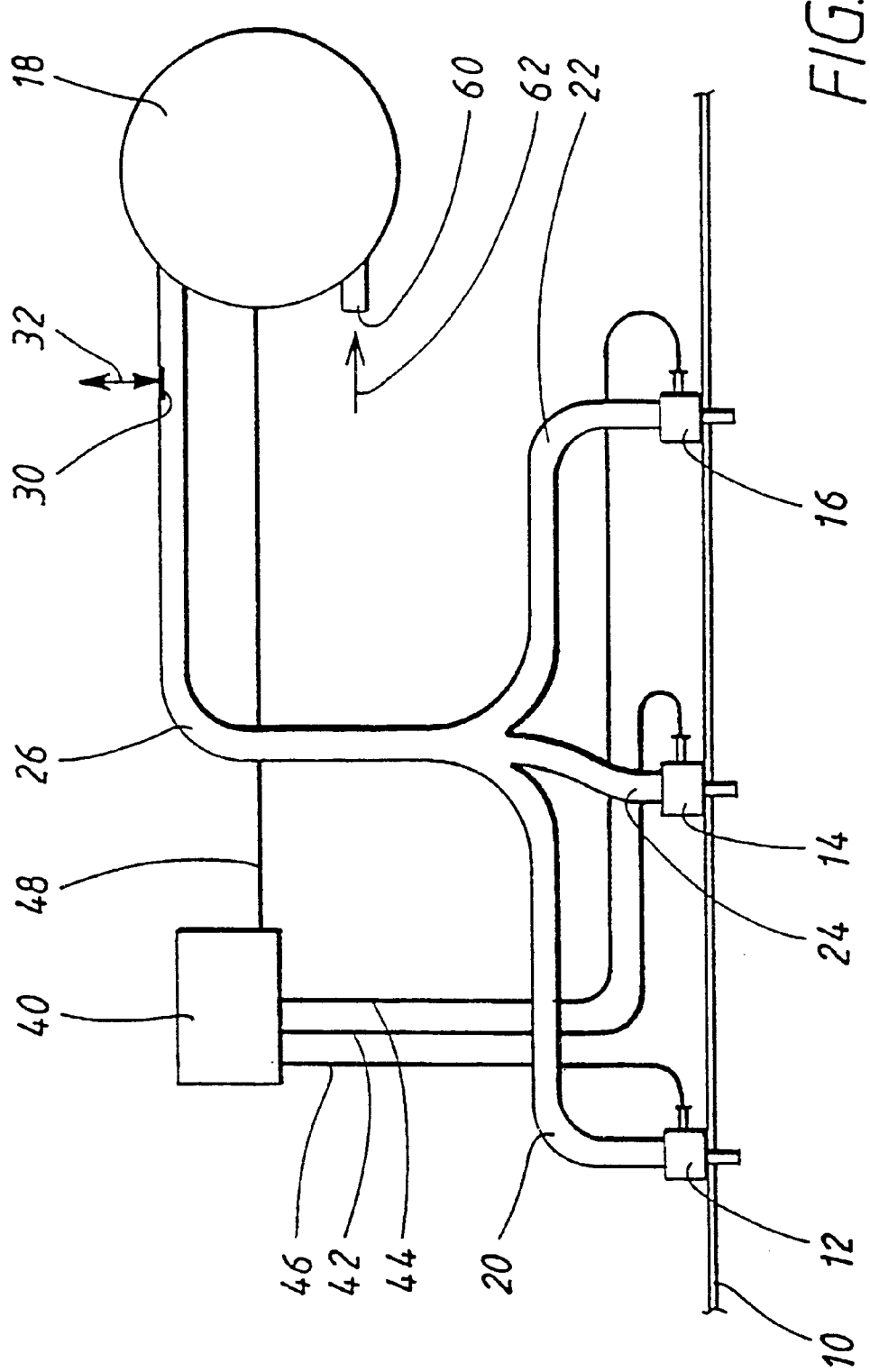
FIG. 1 is a front, schematic representation of apparatus for testing sensors.

Referring to the drawings, FIG. 1 schematically shows apparatus for testing differential pressure sensors, the apparatus being permanently arranged in a dialysis monitor. The dialysis monitor is shown with only part of its housing. In the housing, or within the housing wall 10, three differential pressure sensors, 12, 14, and 16, are arranged for measuring the pressure in blood conduits (not shown).

It is to be noted, that the differential pressure sensors, 12, 14, and 16, can be arranged in a circuit or on a printed circuit within the monitor housing, or each differential pressure sensor can be arranged on its own printed circuit. In this case (not shown), the measurement sides of each of the differential pressure sensors would be connected to terminals on the housing wall in a known manner using appropriate conduits. These connecting conduits may comprise blood filters in order to prevent contamination of the sensors, and thus endangerment of the following patient if the blood conducting tubes leak.

The differential pressure sensors, 12, 14, and 16, each comprise a tube connection on their reference side, which lies inside the housing 10. The tube connection 20 of the differential pressure sensor 12 is connected with an end of a connecting tube 26, as is the tube connection 24 of the differential pressure sensor 14, and the tube connection 22 of the differential pressure sensor 16. This connecting tube 26 leads to a peristaltic pump 18, and is inserted in the peristaltic pump in such a manner that a suction opening 60 at the other end of the connecting tube 26 lies free. The differential pressure sensors, 12, 14, and 16, are, furthermore, connected to a control unit or monitoring unit 40 by means of electric leads, 42, 44, and 46. The peristaltic pump 18 is also connected to the control, or monitor, unit 40 by means of an electric lead 48.

In order to test the differential pressure sensors, 12, 14, and 16, the peristaltic pump 18 is started under the control of control unit 40. It thus sucks air through the suction opening 60 into the connecting tube 26, as indicated by the arrow 62, and generates an excess pressure in the connecting tube 26. This excess pressure is further carried to the tube connections, 20, 22, and 24, connected with connecting tube 26. The tube connections are each connected to the reference side of the differential pressure sensors, 12, 14, and 16, respectively, so that the generated pressure acts on the reference side of the differential pressure sensors, 12, 14, and 16. The resulting signal supplied by each of the differential pressure sensors, 12, 14, and 16, is sent to the control, or monitoring, unit 40 by means of the electrical leads 42, 44, 46. The control unit, or monitor 40 compares the values supplied by the sensors, 12, 14, and 16, and signals an error when the supplied signals are not equal. When functioning correctly, the sensors, 12, 14, and 16, each supply the same signal to the control, or monitoring, unit 40, as the same pressure acts on the differential pressure sensors, 12, 14, and 16, or rather, their reference side.

After terminating the test of the differential pressure sensors, 12, 14, and 16, the peristaltic pump 18 is turned off under control of the control, or monitoring, unit 40. The stationary, or halted, peristaltic pump 18 closes the suction opening 60 of the connecting tube 26, so that pressure equalisation with the surroundings is not possible through the suction opening 60. Pressure equalisation is necessary, however, in order to reduce the excess pressure in the connecting tube 26 and the tube connections, 20, 22, and 24, and to apply the surrounding, or atmospheric, pressure to the reference side of the differential pressure sensors, 12, 14, and 16. Hence, an equalisation opening 30 is provided in the connecting tube 26, and is dimensioned such that, on the one hand, the predetermined pressure can be applied to the reference side of the differential pressure sensors, 12, 14, and 16, with the peristaltic pump 18 and, on the other, the surrounding pressure can be applied as a reference pressure to the reference side of the differential pressure sensors, 12, 14, and 16. After turning off the peristaltic pump 18, air escapes out of the connecting tube 26 through the equalisation opening 30. Thus, pressure equalisation occurs through the equalisation opening 30 between the surroundings and the reference side of the differential pressure sensors, 12, 14, and 16, as shown by arrow 32.

Figure 2:
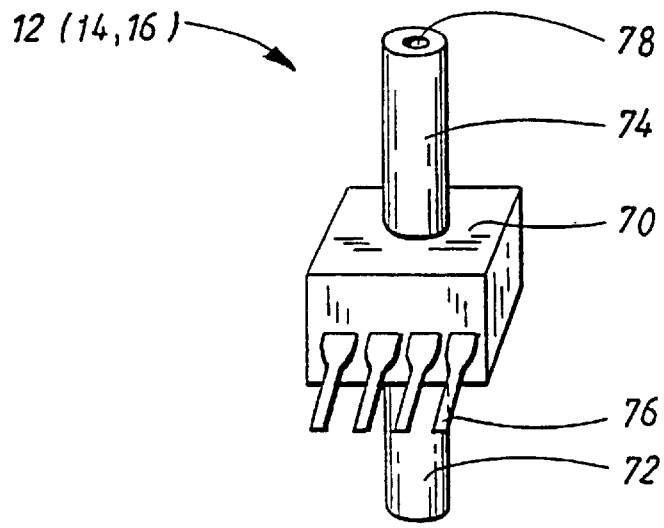
FIG. 2 is a front, perspective view of a sensor used in the apparatus shown in FIG. 2.

In FIG. 2 a three-dimensional side view of one of the piezorestrictive differential pressure sensors, 12, 14, and 16, used in the apparatus is shown. The sensor 12 (14, 16) comprises a sensor housing 70, in which a piezorestrictive element is arranged. A connection support 74 is arranged on one side of the sensor housing 70 and comprises an opening 78, through which a connection is established between the reference side of the piezorestrictive element and the surrounding atmosphere. On the opposite side, the sensor housing 70 comprises a connection support 72, formed in the same way, which is connected to the measurement side of the piezorestrictive element. The sensor housing 70 further comprises a row of contact pins 76 that are electrically connected to the piezoerestrictive element inside the sensor housing 70. A connection to the control, or monitoring, unit 40 is established by means of these contact pins 76 through electrical leads, as shown in FIG. 1.

As is also shown in FIG. 1, the tube connection 20 (or the tube connection 24 or 26) is connected to the connection support 74, so that a predetermined pressure can be applied to the reference side of the piezorestrictive element within the sensor housing 70 by means of the connecting tube 26 and the peristaltic pump 18, as described in detail.

The connection support 72, which is connected to the measurement side of the piezorestrictive element, is connected to the blood carrying conduits, that are not shown here, in a known manner. In the embodiment described above but not shown here, in which the sensors are arranged in a circuit, or a printed circuit, within the housing, the connection support 72 is connected with terminals arranged on the housing wall by means of the connecting conduits, and the terminals are, in turn, connected to the blood-carrying conduits.

Figure 3:
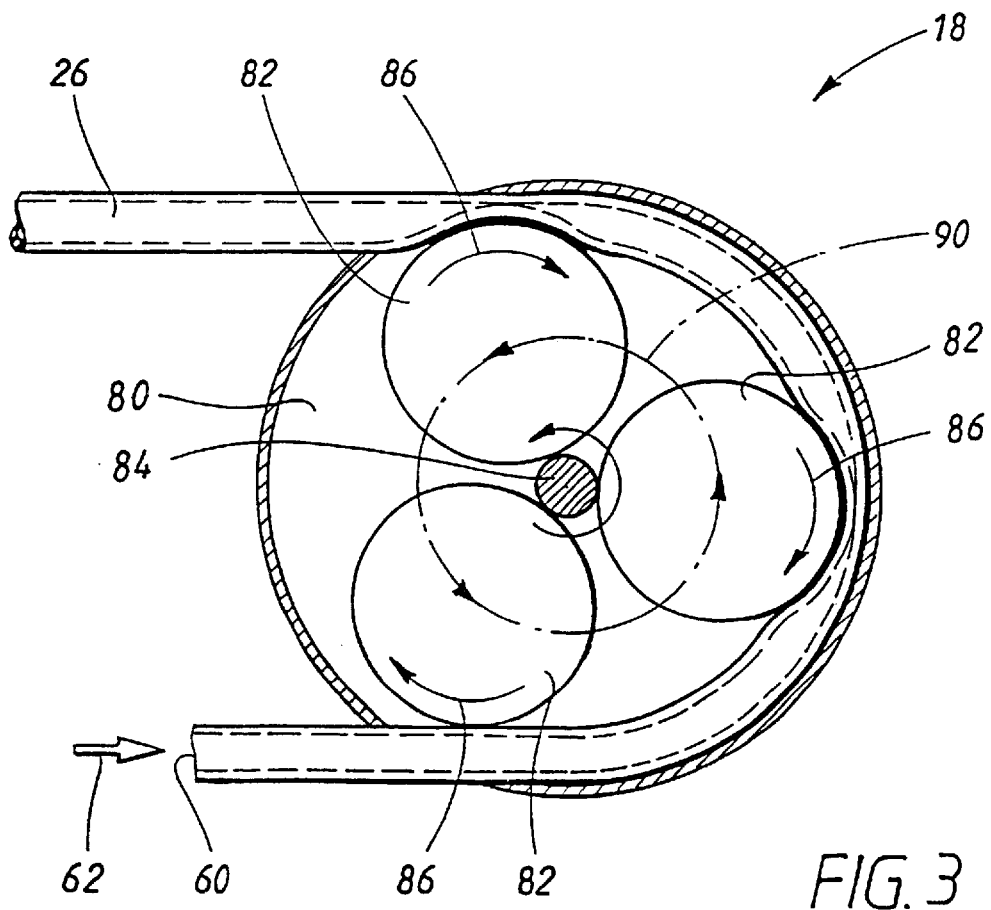
FIG. 3 is a top, elevational, schematic representation of a peristaltic pump utilized in the apparatus of the present invention.

FIG. 3 shows a schematic view of the peristaltic pump 18. The peristaltic pump 18 comprises a pump housing 80, on which is arranged a motor, of which only the motor axle 84 is shown. Moreover, there are provided three freely rotating rolls 82, which are in direct contact with the motor axle 84 and are driven by same. The connecting tube 26 is laid in the peristaltic pump 18, or the pump housing 80, in such a way, that it can be squashed between the rolls 82 and the wall of the pump housing 80.

In order to generate excess pressure in the connecting tube 26, the peristaltic pump 18 is started under control of the control, or monitoring, unit 40 (not shown). The motor axle 84 thus turns in the direction indicated by arrow 88. This causes rotation of the rolls 82 freely mounted in the pump housing 80 in the opposite direction, as indicated by arrow 86. As a result, the rolls 82 revolve within the pump housing 80 in a counter-clockwise direction, as shown by the dashed line with arrow 90 and, at the same time, squash the connecting tube 26 against the wall of the pump housing 80, causing the suction of air through the suction opening 60, as shown by arrow 62.

The thus generated excess pressure in the connecting tube 26 is applied by means of the tube connections, 20, 22, and 24, to the reference sides of the differential pressure sensors, 12, 14, and 16, for testing the latter, as described above in detail. After testing the differential pressure sensors, the peristaltic pump 18 is turned off; the rolls 82 then close the connecting tube 26 towards the suction opening 60. An equalisation of pressure with the surroundings then occurs through the equalisation opening 30, so that the surrounding pressure can reach the reference sides of the piezorestrictive elements of the sensors, 12, 14 and 16, as a reference pressure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for testing a plurality of differential pressure sensors, each of the plurality of differential pressure sensors including a reference side and a measurement side, the method comprising:

applying a first pressure having a first predetermined value to the reference side of the plurality of differential pressure sensors, the first predetermined value being either a positive pressure value or a negative pressure value;

measuring a first set of output values from the measurement side for each of the plurality of differential pressure sensors;

comparing the first set of output values;

applying a second pressure having a second predetermined value to the reference sensor side of the plurality of differential pressure sensors, the second predetermined value being the negative pressure value if the first predetermined value is the positive pressure value or the second predetermined value being the positive pressure value if the first predetermined value is the negative pressure value;

measuring a second set of output values from the measurement side for each of the plurality of differential pressure sensors; and comparing the second set of output values.

2. A method for testing a plurality of differential pressure sensors, each of the plurality of differential pressure sensors including a reference side and a measurement side, the method comprising:

applying a pressure having a predetermined value to the reference side of the plurality of differential pressure sensors;

measuring output values from the measurement side for each of the plurality of differential pressure sensors; and comparing the output values, wherein the differential pressure sensors are arranged in an apparatus for the extracorporeal treatment of blood.

3. The method of claim 2, wherein the apparatus is a dialysis monitor.

* * * * *

UNITED STATES PATENT AND TRADEMARK OFFICE
CERTIFICATE OF CORRECTION

PATENT NO.    : 6,601,432 B1
DATED         : August 5, 2003
INVENTOR(S)   : Bjorn Ericson and Per-Ola Wictor It is certified that error appears in the above-identified patent and that said Letters Patent is hereby corrected as shown below:

<u>Title page,</u>
Item [74], *Attorney, Agent, or Firm*– Lerner, David, Littenberg, Krumholz & Mentlik, LLP --.

Signed and Sealed this

Sixteenth Day of December, 2003

JAMES E. ROGAN
*Director of the United States Patent and Trademark Office*